(12) United States Patent  (10) Patent No.: US 7,794,408 B2
Binette et al.  (45) Date of Patent: Sep. 14, 2010

(54) TISSUE COLLECTION DEVICE AND METHODS

(75) Inventors: Francois Binette, Weymouth, MA (US); Julia Hwang, Wayland, MA (US); Keith M. Orr, Boston, MA (US); Steve Lepke, Wakefield, MA (US); Eric Hyman, Ashland, MA (US); Ashley Perkins, Natick, MA (US)

(73) Assignee: Ethicon, Inc., Somerville, NJ (US)

(*) Notice: Subject to any disclaimer, the term of this patent is extended or adjusted under 35 U.S.C. 154(b) by 553 days.

(21) Appl. No.: 10/402,266

(22) Filed: Mar. 28, 2003

(65) Prior Publication Data

US 2004/0193071 A1 Sep. 30, 2004

(51) Int. Cl.
*A61B 10/00* (2006.01)

(52) U.S. Cl. ....................... 600/562; 604/187

(58) Field of Classification Search ............... 600/562, 600/563, 572, 573, 576, 577, 578, 579; 604/187, 604/198, 207, 218, 237, 119
See application file for complete search history.

(56) References Cited

U.S. PATENT DOCUMENTS

| | | | | |
|---|---|---|---|---|
| 3,604,417 A | * | 9/1971 | Stolzenberg | 604/131 |
| 3,698,561 A | * | 10/1972 | Babson | 210/445 |
| 3,810,545 A | * | 5/1974 | Filz et al. | 210/198.2 |
| 3,814,079 A | * | 6/1974 | Le Roy, Sr. | 600/577 |
| 4,366,822 A | | 1/1983 | Altshuler | |
| 4,469,153 A | * | 9/1984 | Morrisette | 141/364 |
| 4,553,553 A | * | 11/1985 | Homann et al. | 600/562 |
| 4,960,130 A | * | 10/1990 | Guirguis | 600/573 |
| 5,077,012 A | * | 12/1991 | Guirguis | 422/58 |
| 5,108,381 A | * | 4/1992 | Kolozsi | 604/319 |
| 5,197,483 A | | 3/1993 | Rogalsky et al. | |
| 5,252,301 A | * | 10/1993 | Nilson et al. | 422/225 |
| 5,338,294 A | * | 8/1994 | Blake, III | 604/38 |
| 5,398,690 A | | 3/1995 | Batten et al. | |
| 5,494,044 A | * | 2/1996 | Sundberg | 600/562 |
| 5,551,778 A | * | 9/1996 | Hauke et al. | 366/139 |
| 5,827,305 A | | 10/1998 | Gordon | |
| 5,871,462 A | | 2/1999 | Yoder et al. | |
| 5,913,859 A | | 6/1999 | Shapira | |
| 5,944,686 A | | 8/1999 | Patterson et al. | |

(Continued)

FOREIGN PATENT DOCUMENTS

EP 1389548 2/2004

(Continued)

*Primary Examiner*—Max Hindenburg
*Assistant Examiner*—Rene Towa

(57) ABSTRACT

A biological tissue collection device is provided having a housing with a fluid-retaining inner chamber adapted to retain a bioimplantable, fluid permeable tissue scaffold. The scaffold is preferably retained in the housing in such a way that the scaffold separates the fluid-retaining inner chamber into a first chamber and a second chamber. The collection device further includes a driver mechanism coupled to the housing and effective to create a force within the housing to displace fluid disposed within the second chamber to the first chamber. As the fluid is displaced, any biological tissue deposited on the tissue scaffold is dispersed within the fluid. Removal of the force enables the fluid to return to the second chamber and thereby deposit the tissue onto the tissue scaffold. In an exemplary embodiment, the tissue is deposited evenly onto the tissue scaffold.

36 Claims, 12 Drawing Sheets

U.S. PATENT DOCUMENTS

| | | | |
|---|---|---|---|
| 6,022,354 A | 2/2000 | Mercuri et al. | |
| 6,071,284 A | 6/2000 | Fox | |
| 6,216,573 B1 | 4/2001 | Moutafis et al. | |
| 6,280,398 B1 | 8/2001 | Ritchart et al. | |
| 6,299,763 B1 | 10/2001 | Ashman | |
| 6,375,635 B1 | 4/2002 | Moutafis et al. | |
| 6,451,017 B1 | 9/2002 | Moutafis et al. | |
| 6,485,436 B1 | 11/2002 | Truckai et al. | |
| 6,537,567 B1 | 3/2003 | Niklason et al. | |
| 6,572,578 B1 | 6/2003 | Blanchard | |
| 6,736,799 B1 | 5/2004 | Erbe et al. | |
| 6,878,338 B2 * | 4/2005 | Taylor et al. | 422/61 |
| 6,921,380 B1 * | 7/2005 | Epstein et al. | 604/82 |
| 7,115,100 B2 | 10/2006 | McRury et al. | |
| 2001/0043918 A1 | 11/2001 | Masini et al. | |
| 2002/0029055 A1 | 3/2002 | Bonutti | |
| 2002/0082631 A1 | 6/2002 | Bonutti | |
| 2002/0091403 A1 | 7/2002 | Bonutti | |
| 2002/0091406 A1 | 7/2002 | Bonutti | |
| 2002/0099401 A1 | 7/2002 | Bonutti | |
| 2002/0161449 A1 | 10/2002 | Muschler | |
| 2003/0114936 A1 | 6/2003 | Sherwood et al. | |
| 2004/0142861 A1 | 7/2004 | Mansbridge | |

FOREIGN PATENT DOCUMENTS

| | | |
|---|---|---|
| WO | WO96/01135 | 1/1996 |
| WO | WO 99/59500 A2 | 11/1999 |
| WO | WO 00/41648 | 1/2000 |
| WO | 02089722 A1 | 11/2002 |

* cited by examiner

TISSUE COLLECTION DEVICE AND METHODS

FIELD OF THE INVENTION

The present invention relates generally to devices and methods for preparing a tissue scaffold.

BACKGROUND OF THE INVENTION

Bone grafts are often used to treat fractures, gaps in bones caused by trauma or infection, revision joint surgery, and oral/maxillofacial surgery. Bone grafts provide a framework into which the host bone can regenerate and heal. Once implanted, the bone cells weave into and through the porous microstructure of the bone graft to support the new tissue, blood cells and soft tissue as they grow to connect fractured bone segments.

The loss or failure of tissue is one of the most frequent and costly problems in human health care. In recent years, grafting has evolved from the initial autograft and allograft preparations to biosynthetic and tissue-engineered living replacements. Tissue engineering enables the growth of transplantable functional tissue replacements starting from samples of autologous cells of the patient. The cells are obtained by harvesting tissue from a patient using a biopsy and then cells are extracted from the tissue sample and cultured to the appropriate numbers in the laboratory. These living cells are then placed in a three-dimensional natural or synthetic scaffold or matrix, and are kept under tissue specific culture conditions to ensure differentiation and tissue maturation. If provided with the appropriate conditions and signals, the cells will secrete various matrix materials to create an actual living tissue that can be used as a replacement tissue to be implanted back into the defective site in the patient.

Current tissue engineering procedures involve a multi-step process. First, a biopsy is performed to remove a tissue sample from a patient's body. A variety of biopsy devices are well known in the art. U.S. Pat. No. 6,375,635 of Moutafis et al., for example, discloses a biopsy device that employs a high-pressure fluid jet that is effective to cut and retrieve a tissue sample. Once the biopsy procedure is complete, the tissue sample is then sent to a laboratory, where the tissue is prepared for cell isolation. The isolated cells can then be placed into a three-dimensional scaffold for subsequent growth and eventually implantation back into the patient.

While current procedures have proven effective, they can be very time-consuming and costly. Accordingly, there exists a need for more efficient and effective methods for preparing a tissue scaffold.

SUMMARY OF THE INVENTION

The present invention generally provides a biological tissue collection device having a housing with a fluid-retaining inner chamber adapted to retain a biological implant, such as a bioimplantable, fluid permeable tissue scaffold in such a way that the scaffold separates the fluid-retaining inner chamber into a first chamber and a second chamber. Preferably, when a tissue scaffold is disposed within the housing, the first chamber is disposed upstream of the scaffold and the second chamber is disposed downstream of the scaffold. The device further includes a driver mechanism coupled to the housing and effective to create a force within the housing to displace fluid disposed within the second chamber to the first chamber and thereby disperse any biological tissue deposited on the tissue scaffold within the fluid. Removal of the force enables the fluid to return to the second chamber and thereby deposit the biological tissue onto the tissue scaffold. The tissue is preferably evenly distributed onto the scaffold.

The driver mechanism used with the device can have a variety of configurations. In one embodiment, the driver mechanism is a plunger coupled to the first chamber and effective to create a vacuum force to pull fluid from the second chamber into the first chamber. The driver mechanism can optionally be formed integrally with the first chamber such that the first chamber is movable between a first position and a second position to create a vacuum force to draw fluid from the second chamber into the first chamber. In another embodiment, the driver mechanism is coupled to the second chamber and is effective to create a force to push fluid from the second chamber into the first chamber. A variety of driver mechanisms can be used with the present invention, including, for example, one or more plungers, a vacuum pump, a charged gas cylinder, or any other device effective to drive fluid through the collection device.

In one embodiment, the device includes a jet plate disposed within the second chamber that is movable between an original position, in which the jet plate is positioned a distance apart from the tissue scaffold, and a second position, in which the driver mechanism applies a force that causes the jet plate to contact the tissue scaffold. The jet plate, when disposed in the second position, is preferably effective to apply pressure to a surface of the tissue scaffold to force any air bubbles formed on the tissue scaffold to flow into the first chamber. The jet plate can have a variety of configurations, and in one embodiment it is a body having at least one channel extending therethrough for allowing fluid to flow through the jet plate. The channel(s) can be oriented at an angle and can extend between upper and lower surfaces of the jet plate. Preferably, the channel(s) extends from a perimeter of the lower surface of the jet plate to a center of the upper surface of the jet plate.

In yet another embodiment of the present invention, the second chamber can include an overflow mechanism effective to allow any excess fluid disposed within the second chamber to be released. The overflow mechanism can be in the form of a channel, a port, a valve, or any other device that allows fluid to flow therethrough.

The present invention also provides a retaining member effective to retain a tissue scaffold within the chamber. The retaining member can comprise a wire mesh disposed within the housing between the first and second chambers. The wire mesh is adapted to seat a tissue scaffold. Alternatively, or in addition, the retaining member can comprise a clamping ring effective to clamp an outer perimeter of a tissue scaffold. In use, the retaining member is preferably removably disposed within the inner chamber of the housing. The housing can include a transverse slot formed therein for removably receiving the retaining member.

In another embodiment of the invention, the housing can comprise a first portion defining the first inner chamber, and a second portion defining the second inner chamber. The first and second portions are adapted to removably mate to one another and to receive a tissue scaffold therebetween. The first and second portions can optionally define a retaining member for seating a tissue scaffold.

In yet another embodiment of the present invention, a biological tissue collection device is provided having a housing with a proximal chamber, a distal chamber, and a tissue scaffold retaining member disposed therebetween. A driver mechanism is coupled to the proximal chamber and is effective to create a fluid driving force within the first and second chambers. The device also includes a driver release mechanism formed in one of the first and second chambers and that is effective to release the force applied by the driver mechanism. The device can optionally include a jet plate disposed within the distal chamber that, when the driver mechanism is activated, is effective to control fluid flow.

Methods of preparing a tissue scaffold are also provided.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
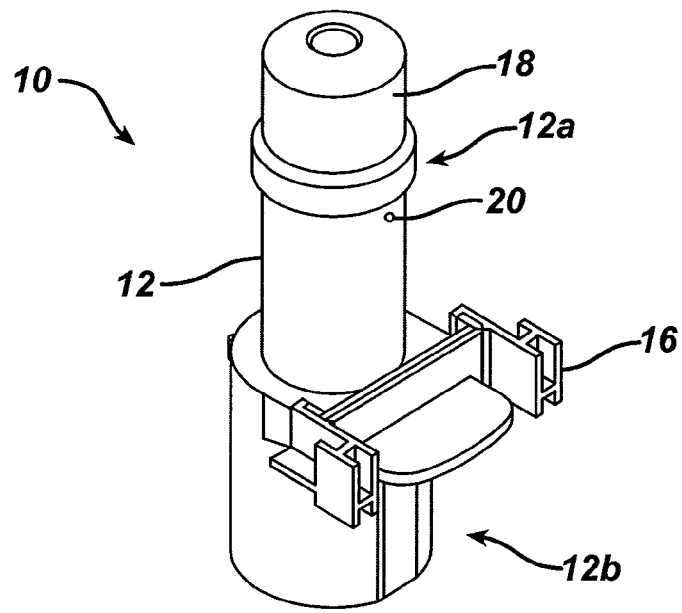
FIG. 1A is a perspective view of one embodiment of a tissue collection device according to the present invention.

In general, the present invention provides a biological tissue collection device having a housing with a fluid-retaining inner chamber adapted to retain a biological implant, such as a bioimplantable, fluid permeable tissue scaffold. The scaffold is preferably retained in the housing in such a way that the scaffold separates the fluid-retaining inner chamber into a first chamber and a second chamber. The collection device further includes a driver mechanism coupled to the housing that is effective to create a force within the housing to displace fluid disposed within the second chamber to the first chamber. As the fluid is displaced, any biological tissue deposited on the tissue scaffold is dispersed within the fluid. Removal of the force enables the fluid to return to the second chamber and thereby deposit the tissue onto the tissue scaffold. In an exemplary embodiment, the tissue is deposited evenly onto the tissue scaffold.

A variety of tissue scaffolds 16a are known in the art and can be used with the present invention. The scaffold 16a can be formed using virtually any material or delivery vehicle that is biocompatible, bioimplantable, easily sterilized and that has sufficient structural integrity and/or physical and mechanical properties to effectively provide for ease of handling in an operating room environment and to permit it to accept and retain sutures or other fasteners without substantially tearing. By way of non-limiting example, the scaffold 16a can be in the form of an injectable gel that would set in place at a defect site. In another embodiment, the scaffold can be in the form of a matrix that is formed from a variety of materials, including resorbable materials, non-biological materials, or synthetic materials. Preferably, the scaffold is also pliable so as to allow the scaffold to conform to the shape and dimensions of the target site of implantation. The scaffold can also include a bioabsorbable or bioresorbable component to act as a temporary carrier to improve handling of the implant during transportation. The temporary scaffold would eventually be absorbed and thereby removed after transportation of the implant.

A person having ordinary skill in the art will appreciate that the term "scaffold," or "tissue scaffold," as used herein is intended to include a variety of other biological implants in addition to scaffolds.

The tissue scaffold 16a can optionally include biological agents and/or a protective element, or sheet (not shown), disposed thereon for protecting the scaffold 16a from the distal portion of the plunger 18, and for retaining the tissue sample thereon. The protective element can be formed from virtually any biocompatible material, and in one embodiment, the protective element can be formed using tissue grafts, including an allograft, an autograft, a xenograft, an additional biocompatible scaffold selected from the biocompatible scaffolds disclosed above, and combinations thereof. In another embodiment, the protective element can be a porous mesh, a porous mesh-like material, such as for example, a knit, a weave, a nonwoven, or a thin, perforated elastomeric sheet having pores or perforations to allow tissue ingrowth. The thin, perforated elastomeric sheets are preferably constructed from collagen or silk or blends or copolymers of polylactic acid (PLA), polyglycolic acid (PGA), polycaprolactone (PCL) and polydioxanone (PDO). The type of protective element used can vary according to the desired tissue repair. The protective element can be delivered onto the scaffold 16a prior to use of the collection device 10, or alternatively can be delivered onto the scaffold 16a after the scaffold is prepared. One of more entry ports, similar to entry port 20, can be provided in the housing 12 for allowing biological agents and/or a protective element to be delivered into the proximal chamber 14a without requiring the chamber 14a to be opened.

Figure 1B:
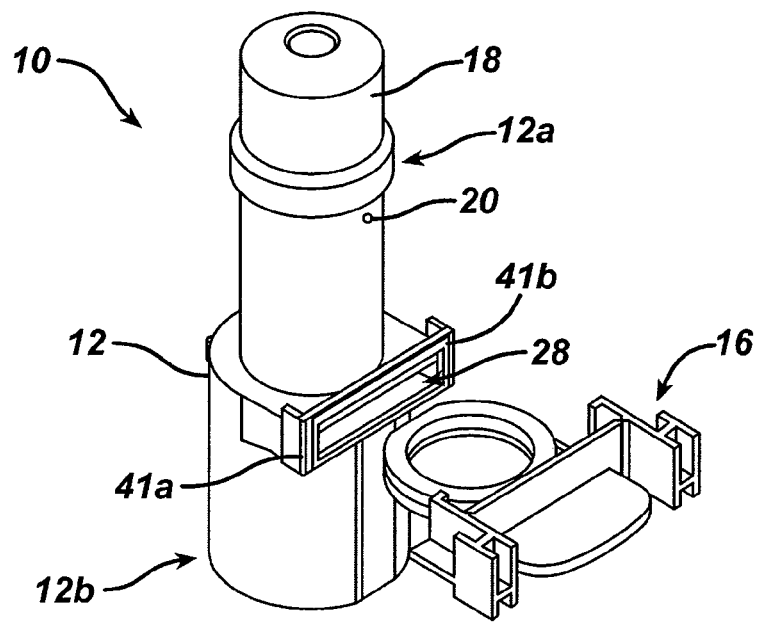
FIG. 1B is a perspective view of the tissue collection device of FIG. 1A having a retaining tray removed therefrom.
Figure 2:
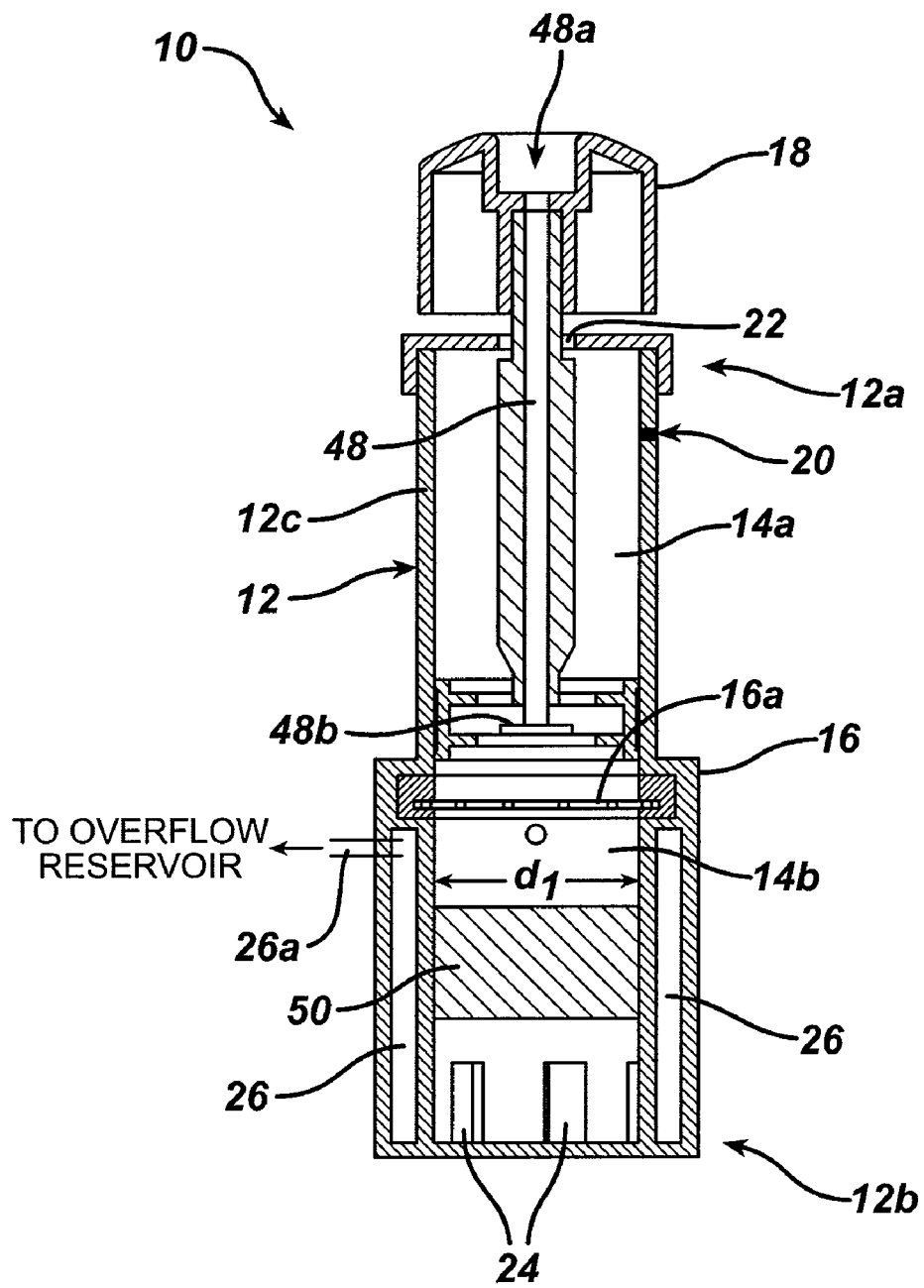
FIG. 2 is a cross-sectional view of the tissue collection device shown in FIG. 1A.

FIGS. 1A, 1B, and 2 illustrate one embodiment of a tissue collection device 10. As shown, the device 10 generally includes a housing 12 having a proximal end 12a, a distal end 12b, and an inner chamber extending therebetween. A scaffold retaining member 16 is removably disposed within the housing 12 between the proximal and distal ends 12a, 12b, and is adapted to retain a bioimplantable, fluid-permeable tissue scaffold 16a therein. The scaffold 16a is effective to separate the inner chamber of the housing 12 into a first, proximal chamber 14a and a second, distal chamber 14b. The device 10 further includes a driver mechanism, e.g., a plunger 18, coupled to the proximal chamber 14a. The plunger 18 is effective to create a vacuum force, when moved in a proximal direction, to draw fluid disposed within the distal chamber 14b up into the proximal chamber 14a. As a result, any tissue disposed on the surface of the tissue scaffold 16a will be dispersed within the fluid in the proximal chamber 14a. Once the plunger 18 is moved proximally past a driver release mechanism, e.g., air flow entry port 20, the force is removed and the fluid is free to flow back into the distal chamber 14b, thereby depositing the tissue back onto the tissue scaffold 16a. The tissue is preferably deposited onto the scaffold 16a in a uniform manner.

The housing 12 can have a variety of configurations, and can have virtually any shape and size. As shown in FIG. 2, the housing 12 has a generally elongate, cylindrical shape and includes a proximal end 12a, a distal end 12b, and a sidewall 12c extending therebetween and defining an inner chamber. The inner chamber includes a proximal chamber 14a and a distal chamber 14b that are separated by a fluid-permeable tissue scaffold 16a. The proximal and distal chambers 14a, 14b can be formed in separate portions of the housing 12 which mate together, or alternatively the housing 12 can be formed from an integral unit such that the proximal and distal chambers 14a, 14b are fixedly mated together to form a single chamber. The proximal end 12a of the housing 12 is adapted to receive the driver mechanism, e.g., plunger 18, and thus can include an opening 22 formed therein. The opening 22 can have any shape and size, and can be a port formed in the housing 12, or alternatively the entire proximal end 12a of the housing 12 can be open. The distal end 12b of the housing 12 forms the base of the device 10, and is therefore preferably substantially planar. The distal end 12b can optionally mate to or include a support to maintain the device 10 in an upright position during use.

The proximal and distal chambers 14a, 14b in the housing 12 are adapted to retain fluid therein. Preferably, the fluid, which includes biological tissue taken from a patient, is introduced into the proximal chamber 14a where it is allowed to flow through the fluid-permeable scaffold 16 into the distal chamber 14b. The biological tissue disposed within the fluid is collected on the scaffold. By way of non-limiting example, fluid can be introduced into the housing 12 through a port formed in the sidewall 12c of the housing 12, through an opening in the proximal end 12a of the housing 12, or through a delivery lumen 48 formed in the driver mechanism 18, as shown in FIG. 2 and as will be discussed in more detail with respect to FIG. 4. The distal chamber 14b can be adapted to hold a particular volume of fluid, and thus can include an overflow mechanism that will allow any excess fluid introduced through the proximal chamber 14a and into the distal chamber 14b to be drained out of the distal chamber 14b. The overflow feature will prevent fluid introduced into the device from remaining in the proximal chamber 14a, and will control the volume of fluid allowed to remain in the distal chamber 14b. In an alternative embodiment (not shown), the fluid can be recycled from the distal chamber 14b back into the proximal chamber 14a, rather than providing an overflow feature for collecting excess fluid. In an exemplary embodiment, the fluid level in the distal chamber 14b will be spaced a distance apart from the tissue scaffold to create an air pocket between the fluid and the scaffold. In use, when the fluid is drawn up into the proximal chamber 14a, the air pocket will remain above the fluid such that the air pocket will prevent the fluid from coming into contact with the driver mechanism 18, thereby preventing any potential damage to the tissue contained within the fluid.

As shown in FIG. 2, distal chamber 14b includes one ore more channels 24 formed in the distal end 12b of the housing 12 that form the overflow feature. The channels 24 communicate with side channels 26 having an outlet port 26a located just distal to the tissue scaffold 16. The position of the outlet port 26a will control the level of fluid allowed to remain in the distal chamber 14b, since the fluid level will not be allowed to rise above the position of the outlet port 26a. The excess fluid flowing through the outlet port 26a can be collected in a reservoir built into the device, or in an external reservoir. The fluid can optionally be allowed to re-circulate into the system. A person having ordinary skill in the art will appreciate that several techniques can be used to control the level of fluid disposed within the system, and the illustrated overflow feature is merely a preferred embodiment.

As previously stated above, the housing 12 is adapted to retain a tissue scaffold 16a between the proximal and distal chambers 14a, 14b. A variety of techniques can be used to position the scaffold 16a within the housing 12. Preferably a retaining member 16 that seats the scaffold 16a is provided and is removably disposed within the housing 12. A transverse slot 28, shown in FIG. 1B, can be formed in the housing 12 for slidably receiving the retaining member 16. The slot 28 should be configured to provide an air-tight seal around the retaining member 16 when the retaining member 16 is fully inserted into the slot 28. While the scaffold is shown disposed within a retaining member, a person having ordinary skill in the art will appreciate that the scaffold can be disposed anywhere within the housing. By way of non-limiting example, the scaffold can be disposed on the driver mechanism 18, or within any other part of the housing that allows tissue to be deposited and re-deposited thereon.

Figure 3A:
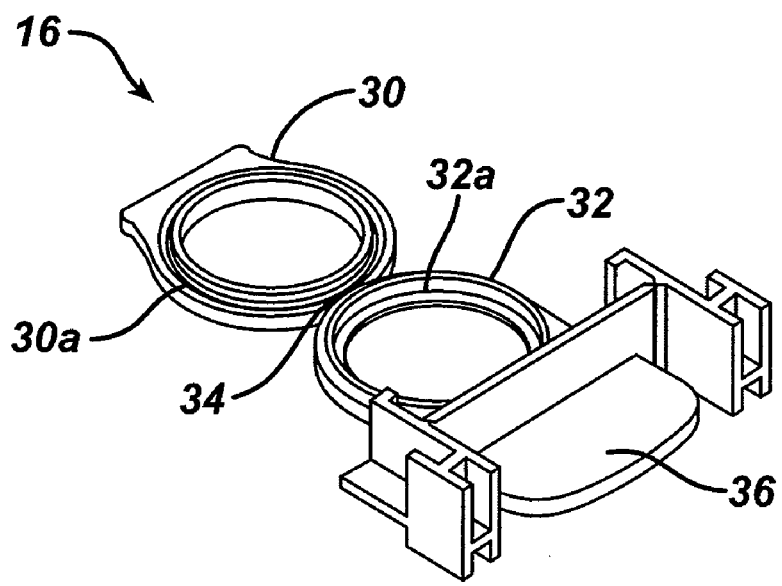
FIG. 3A is a perspective view of the retaining tray of the tissue collection device of FIG. 1A shown in the open state.
Figure 3B:
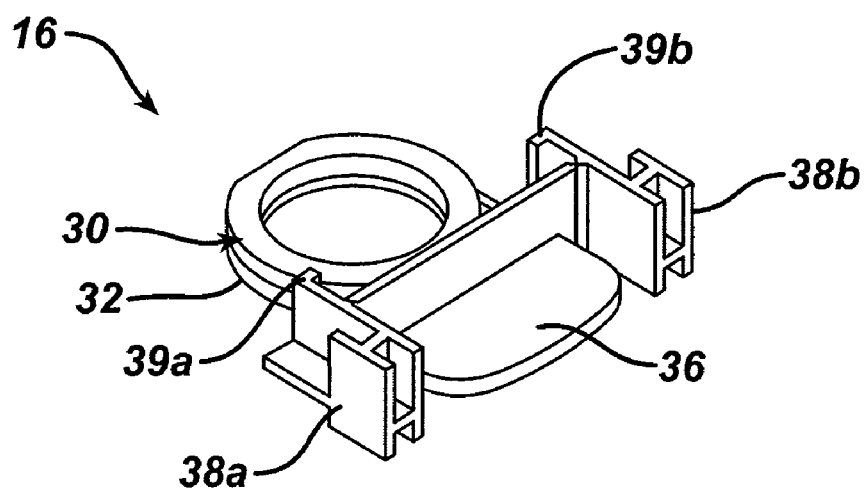
FIG. 3B is a perspective view of the retaining tray of the tissue collection device of FIG. 1A shown in the closed state.

The retaining member 16 can have a variety of configurations, and can be adapted to merely seat a tissue scaffold 16a therein, or it can be adapted to engage and optionally tension the scaffold 16a. As shown in FIGS. 3A and 3B, the retaining member 16 includes an upper portion 30 and a lower portion 32, each having a substantially circular shape with a central opening formed therein. The upper and lower portions 30, 32 are adapted to mate together and engage a perimeter of a tissue scaffold 16a therebetween. The upper and lower portions 30, 32 can each optionally include a retaining ring 30a, 32a formed around the perimeter thereof to facilitate grasping of a tissue scaffold 16a. A variety of techniques can be used to mate the upper portion 30 to the lower portion 32. Preferably, the upper portion 30 is attached to the lower portion 32 by way of a hinge 34 to facilitate ease of use. Moreover, a snap-fit engagement or similar mating technique can be provided to temporarily lock the portions 30, 32 together around a tissue scaffold 16a.

The scaffold retaining member 16 can also include a handle 36 to facilitate insertion and removal of the device 16 into the slot 28 formed in the housing 12. The handle 36 can have virtually any configuration. As shown in FIGS. 3A and 3B, the handle 36 is a substantially planar member that extends in the same plane as the upper and lower portions 30, 32. The handle 36 is mated to the lower portion 32 along a side opposite to the location of the hinge 34. The retaining member 16 can also include an engagement mechanism to secure the retaining member 16 within the slot 28 in the housing 12. Still referring to FIGS. 3A and 3B, the engagement mechanism is in the form of opposed T-shaped rails 38a, 38b having flexible tabs 39a, 39b formed therein. The tabs 39a, 39b are adapted to snap around ridges 41a, 41b formed on opposed outer edges of the slot 28. A person having ordinary skill in the art will appreciate that a variety of techniques can be used to mate the retaining member 16 to the housing 12.

Figure 4:
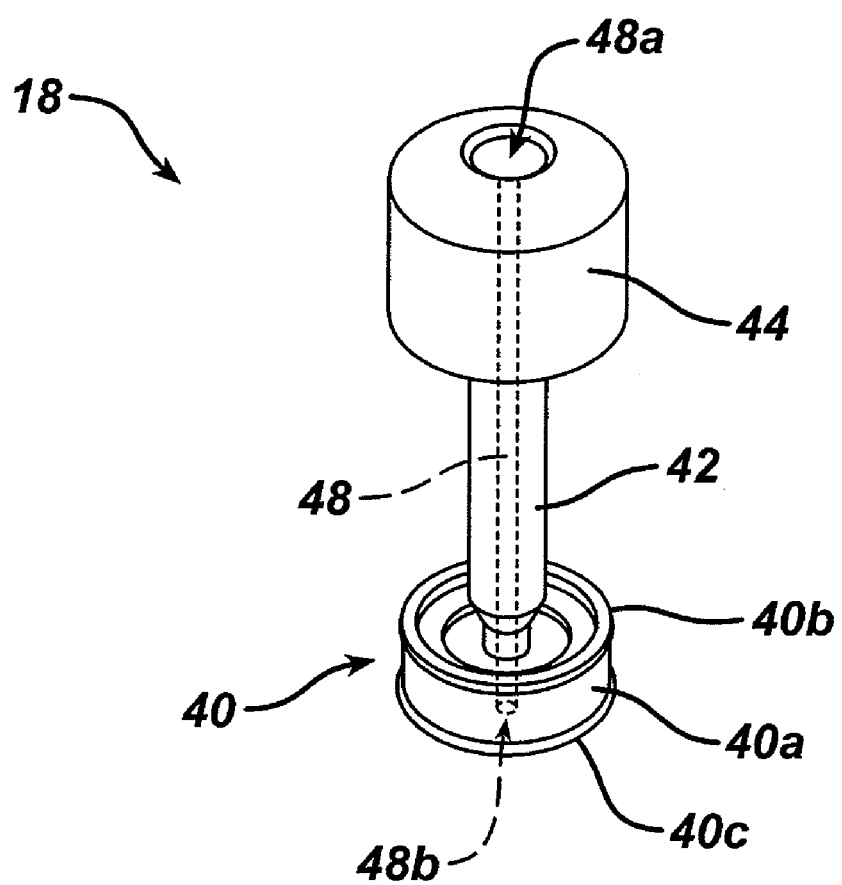
FIG. 4 is a perspective view of the driver mechanism of the tissue collection device of FIG. 1A.

The tissue collection device further includes a driver mechanism coupled to the housing and effective to create a force to displace fluid disposed within the second, distal chamber 14b into the first, proximal chamber 14a. The driver mechanism can be coupled to either chamber 14a, 14b. FIGS. 2 and 4 illustrate one embodiment of a plunger 18 disposed within the proximal chamber 14a and that is effective to create a vacuum force within the chambers 14a, 14b to draw fluid from the distal chamber 14b up into the proximal chamber 14a. The plunger 18 includes a sealing member 40, a shaft 42, and a handle member 42. The sealing member 40, which can have a variety of configurations, should have a shape and size adapted to fit within the proximal chamber 14a and to provide an airtight seal with the sidewall 12c of the chamber 14a. As shown in FIG. 4, the sealing member 40 is formed from a cylindrical wall 40a having o-rings 40a, 40b formed on opposed ends of the wall 40a. The o-rings 40a, 40b provide an airtight seal with the sidewall 12c of the chamber 14a. The shaft 42 extends proximal from the sealing member 40 and is mated to the handle member 44, which allows the plunger 18 to be grasped and manipulated.

The handle 44 can be used to manually move the plunger 18 between a proximal position, in which the sealing member 40 is positioned at the proximal end of the proximal chamber 14a, and a distal position, in which the sealing member 40 is substantially disposed within the proximal chamber 14a and is positioned adjacent the tissue scaffold 16a. Alternatively, the plunger 18 can include a mechanical device, such as a spring, for driving the plunger 18 between the proximal and distal positions at a substantially constant rate. Preferably, a compression spring (not shown) is disposed within or around the shaft 42 and is mated to the proximal end 12a of the housing. In use, the plunger 18 is moved distally within the proximal chamber 14a, thereby expanding the compression spring. A locking mechanism (not shown) can be provided for temporarily locking the plunger 18 in the distal position. Once the locking mechanism is released, the spring is effective to pull the plunger in a proximal direction thereby pulling fluid from the distal chamber 14b into the proximal chamber 14a. In an exemplary embodiment, the plunger is moved at a constant rate of 1 inch per second. A person having ordinary skill in the art will appreciate that virtually any driver mechanism can be used to drive fluid through the collection device 10.

The plunger 18 can also optionally include a delivery lumen 48 extending therethrough, as shown in FIGS. 2 and 4, for delivering fluid into the chambers 14a, 14b. The delivery lumen 48 extends through the handle member 44, the shaft 42, and the sealing member 40. The proximal opening 48a of the lumen 48 preferably includes a cap or other device for sealing the lumen 48 once the fluid is delivered into the chambers 14a, 14b. The delivery lumen 48 can also optionally be adapted to control the delivery rate of fluid flow into the chambers 14a, 14b. By way of non-limiting example, a deflection plate (not shown) or similar device can be disposed at the distal end 48b of the lumen 48 to deflect the fluid flow therethrough. This is particularly effective to prevent damage to tissue contained within the fluid being delivered to the inner chambers 14a, 14b. A person having ordinary skill in the art will appreciate that the fluid can be delivered into the chambers 14a, 14b using a variety of techniques, and that it does not need to be delivered through the plunger 18.

In use, a tissue-containing fluid is delivered into the proximal chamber 14a, and the plunger 18 is moved into the distal position. The fluid is free to flow through the tissue scaffold 16a into the distal chamber 14b, while tissue present within the fluid is collected on the scaffold 16a. The chambers 14a, 14b and/or the delivery lumen 48 in the plunger 18 are then sealed to create an airtight system. The locking mechanism, if provided, can then be released thereby allowing the plunger 18 to move in a proximal direction. As previously stated, the plunger 18 can be moved either manually or mechanically. Movement of the plunger 18 is effective to create a vacuum force within the chambers 14a, 14b which pulls the fluid within the distal chamber 14b up through the tissue scaffold 16a and into the proximal chamber 14a. This fluid flow causes any tissue disposed on the surface of the tissue scaffold 16a to be dispersed within the fluid in the proximal chamber 14a. Once the sealing member 40 of the plunger 18 is moved proximally beyond the air flow entry port 20, air is allowed to enter the chamber 14a and thereby release the vacuum force. The fluid is then free to flow back into the distal chamber 14b through the tissue scaffold 16a, thereby re-depositing the tissue back onto the scaffold. Preferably, the tissue is evenly distributed onto the scaffold 16a. Once the tissue is deposited back onto the tissue scaffold, other fluids can be introduced into the proximal chamber 14a of the housing 12 to further prepare the scaffold. By way of non-limiting example, fibrin glue can be delivered into the housing 12 through the plunger 18 or through a port formed in the housing to retain the tissue on the tissue scaffold.

The tissue collection device 10 can optionally include a mechanism to facilitate the even distribution of tissue back onto the tissue scaffold 16a. As shown in FIGS. 2 and 5A-5C, a jet plate 50 can be disposed within the distal chamber 14b. The jet plate 50 can have a variety of shapes and sizes, but it is preferably adapted to control the flow of fluid from the distal chamber 14b to the proximal chamber 14a. The jet plate 50 can also be effective to prevent the formation of, or remove any, air bubbles on the distal surface of the tissue scaffold 16a. Any air bubbles formed on the tissue scaffold can affect the flow of fluid, and as a result could cause the tissue dispersed within the fluid in the proximal chamber to be redistributed onto the tissue scaffold 16a in an uneven manner.

Figure 5A:
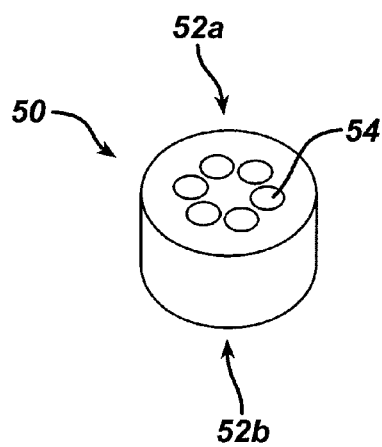
FIG. 5A is a top perspective view of a jet plate according to one embodiment of the present invention.
Figure 5B:
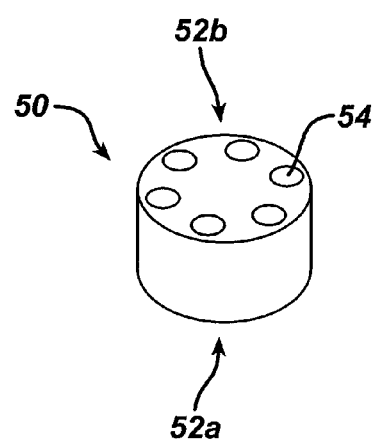
FIG. 5B is a bottom perspective view of the jet plate shown in FIG. 5A.
Figure 5C:
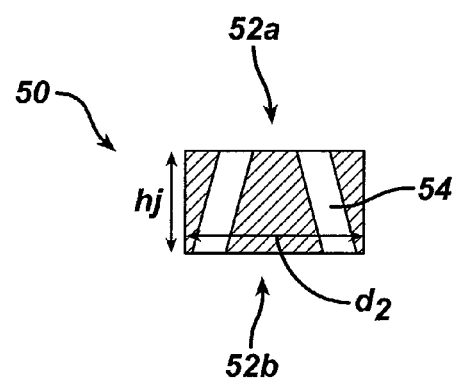
FIG. 5C is a cross-sectional view of the jet plate shown in FIG. 5A.

As shown in FIGS. 5A-5C, the jet plate 50 has a generally cylindrical shape and includes a proximal end 52a and a distal end 52b. The size of the jet plate 50 can vary, but preferably the jet plate 50 has a diameter $d_2$ slightly smaller than the diameter $d_1$ (shown in FIG. 2) of the distal chamber 14b to allow the jet plate 50 to travel vertically, but not horizontally, within the distal chamber 14b. The height $h_j$ of the jet plate 50 can also vary, but in an exemplary embodiment the jet plate has a height $h_j$ that allows it to be positioned about ½" from the tissue scaffold 16a when the jet plate 50 is resting on the distal end of the distal chamber 14b.

The jet plate 50 is preferably substantially solid, but includes one or more lumens 54 extending therethrough between the proximal and distal ends 52a, 52b for allowing fluid to flow through the jet plate 50. The jet plate 50 can include any number of lumens 54 extending through the jet plate 50 at any location. In an exemplary embodiment, however, the lumens 54 extend from a perimeter of the distal end 52b to the center of the proximal end 52a of the jet plate 50, as shown in FIGS. 5A-5C. The angled configuration of the lumens 54 is effective to redirect the flow of fluid therethrough, and to cause agitating of the fluid above the tissue scaffold 16a. Each lumen 54 can also vary in size to control the rate of fluid flow therethrough.

In use, as fluid is drawn from the distal chamber 14b into the proximal chamber 14a, the force created by the plunger 18 causes the jet plate 50 to move proximally within the distal chamber 14b as fluid flows through the lumens 54. The jet plate 50 eventually comes into contact with the tissue scaffold 16a which, as a result, causes any air bubbles formed on the tissue scaffold 16a to flow through the scaffold and into the proximal chamber 14a. Once the force created by the plunger 18 is released, the jet plate 50 is free to drop back down and return to the distal end of the distal chamber 14b. A person having ordinary skill in the art will appreciate that the jet plate 50 can have a variety of configurations, and that a variety of other techniques can be used to control the fluid flow through the device, and to remove air bubbles from the surface of the tissue scaffold 16a.

Figure 6A:
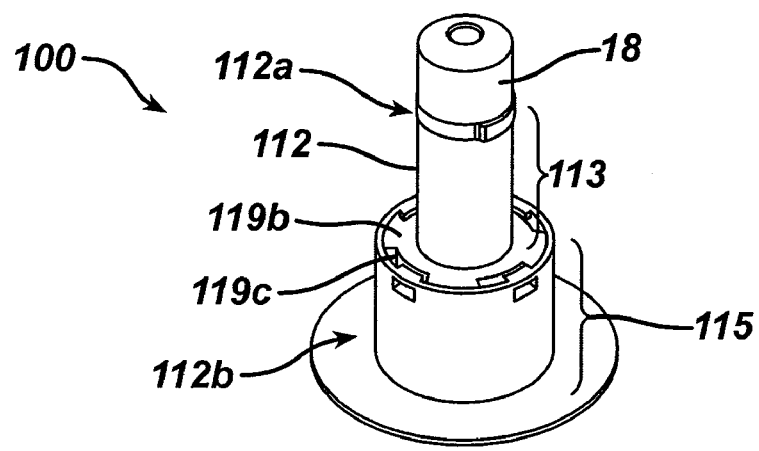
FIG. 6A is a perspective view of another embodiment of a tissue collection device according to the present invention.
Figure 6B:
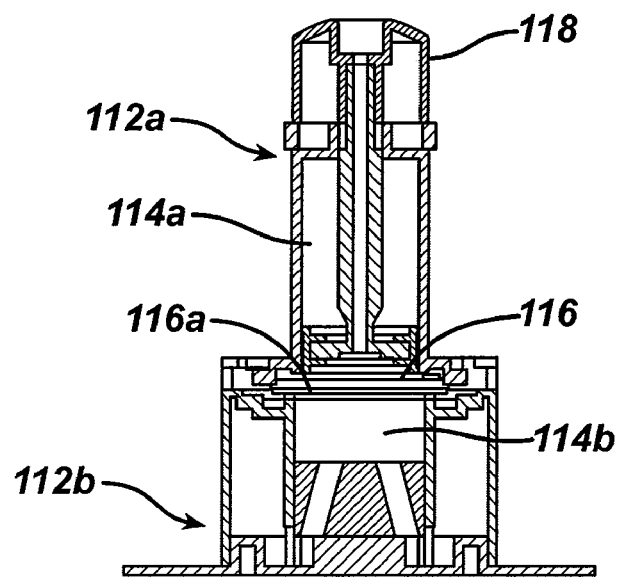
FIG. 6B is a cross-sectional view of the tissue collection device shown in FIG. 6A.

FIGS. 6A-8 illustrate yet another embodiment of a tissue collection device 100 according to the present invention. As shown, device 100 is similar to device 10 shown in FIGS. 1-5C, and thus similar elements are designated by the same reference number with the prefix "1." As shown in FIGS. 6A and 6B, the device 100 generally includes a housing 112 having proximal and distal ends 112a, 112b, a proximal chamber 114a, and a distal chamber 114b formed therein. While the device 100 is similar in most respects to device 10 described above with respect to FIGS. 1-5C, the proximal and distal chambers 114a, 114b are removably mated to one another. More particularly, the housing 112 is separated into a proximal portion 113 and a distal portion 115, as shown in FIG. 6A and FIGS. 7A-7C. The portions 113, 115 are removably mated to one another, and allow the tissue scaffold retaining member 116a to be disposed therebetween. The device 100 further includes a driver mechanism, e.g., plunger 118, coupled to the proximal portion 113 of the housing 112.

Figure 7A:
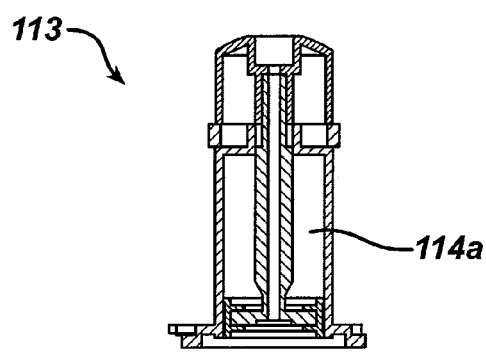
FIG. 7A is a cross-sectional view of the proximal portion of the tissue collection device shown in FIG. 6A.
Figure 7B:
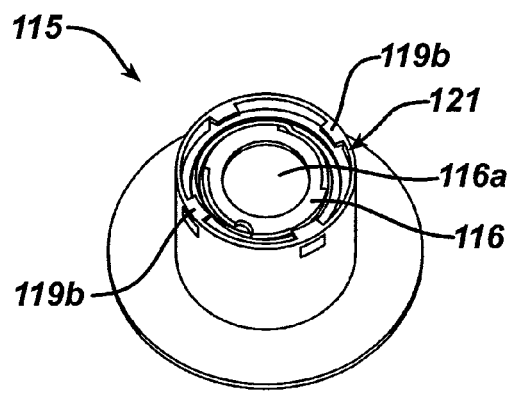
FIG. 7B is a top perspective view of the distal portion of the tissue collection device shown in FIG. 6A.
Figure 7C:
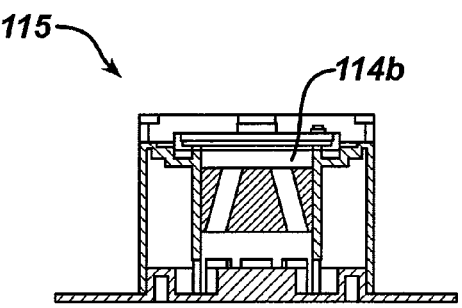
FIG. 7C is a cross-sectional view of the distal portion of the tissue collection device shown in FIG. 7B.

Referring now to FIGS. 7A and 7B, the proximal and distal portions 113, 115 of the housing each include a mating feature formed thereon for allowing the portions 113, 115 to be removably attached to one another. Virtually any mating feature can be provided, but the mating feature should provide an air tight connection between the portions 113, 115. In one embodiment, as shown, the mating feature utilizes a twist-lock connection wherein the distal portion 115 of the housing 112 includes tabs 119b formed thereon that are adapted to engage a rim 119a (FIG. 6A) formed on the proximal portion 113 of the housing 112. The rim 119a includes cut-out features 119c that receive the tabs 119b when the proximal and distal portions 113, 115 are positioned in a first position. The proximal and distal portions 113, 115 can then be rotated with respect to one another to allow the tabs 119b to engage the rim 119a, thereby locking the portions 113, 115 together. In another embodiment (not shown), the portions can snap together, thread together, or otherwise engage one another. A person having ordinary skill in the art will appreciate that virtually any mating technique can be used.

Figure 8:
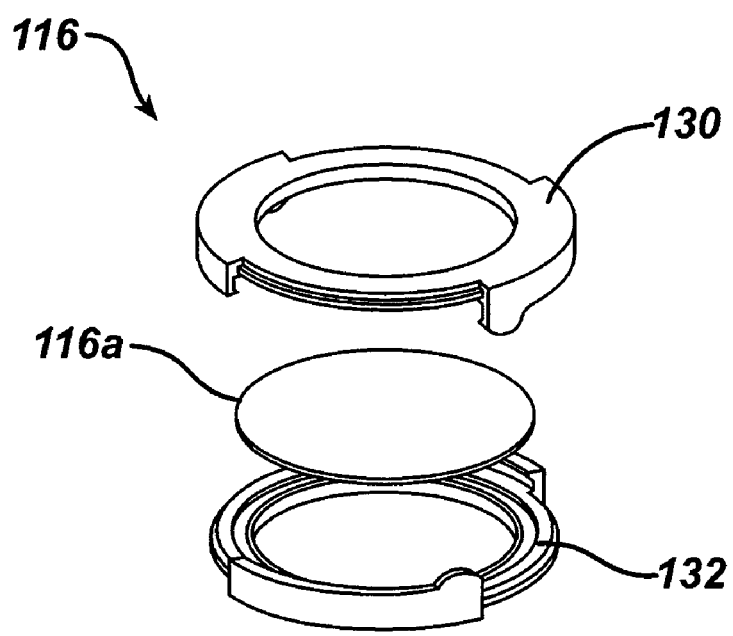
FIG. 8 is a perspective view of a tissue scaffold retaining member shown in a disassembled state according to one embodiment of the present invention.

The scaffold retaining member 116 is adapted to be disposed between the proximal and distal portions 113, 115 of the housing 112. The retaining member 116 can be seated between the portions 113, 115, or can mate to one or both portions 113, 115 using a mating element. In an exemplary embodiment, shown in FIG. 7B, the scaffold retaining member 116 is in the form of a cylindrical tray that sits within an annular groove 121 formed in the distal portion 115. The retaining member 116, which is shown in more detail in FIG. 8, is similar to retaining member 16 described above with respect to FIGS. 3A and 3B and includes upper and lower portions 130, 132. The portions 130, 132, however, are not hingedly connected, but rather snap together to grasp the outer perimeter of a tissue scaffold 116a. The upper and lower portions 130, 132 can mate together using a variety of mating techniques, including, for example, a snap-fit connection, a twist-lock connection, a magnetic connection, and a variety of other connections known in the art. A person having ordinary skill in the art will appreciate that the upper and lower portions 130, 132 do not need to mate to one another, but rather can merely seat within distal portion 115 of the housing. Moreover, a tissue retaining member 116 is not necessarily required with the present invention, but rather the proximal and/or distal portions 113, 115 of the housing can be adapted to directly receive a tissue scaffold 116a. The retaining member 116 is preferably provided, however, to assist in transporting the scaffold 116a prior to and subsequent to use of the device 100.

A person having ordinary skill in the art will appreciate that while FIGS. 1A-8 illustrate collection devices 10, 100 that utilize a plunger 18, 118 coupled to the proximal chamber 14a, 114a of the housing 12, 112, a variety of alternative driver mechanisms can be utilized and the driver mechanism can be coupled to either or both of the proximal and distal chambers 14a, 14b, 114a, 114b. FIGS. 9-13B illustrate additional embodiments of collection devices. The devices are similar to collection device 10 and collection device 100 described above, and thus similar elements are designated by the same reference numbers with the prefer "2" for the embodiment shown in FIG. 9, the prefix "3" for the embodiment shown in FIG. 10, and so on.

Figure 9:
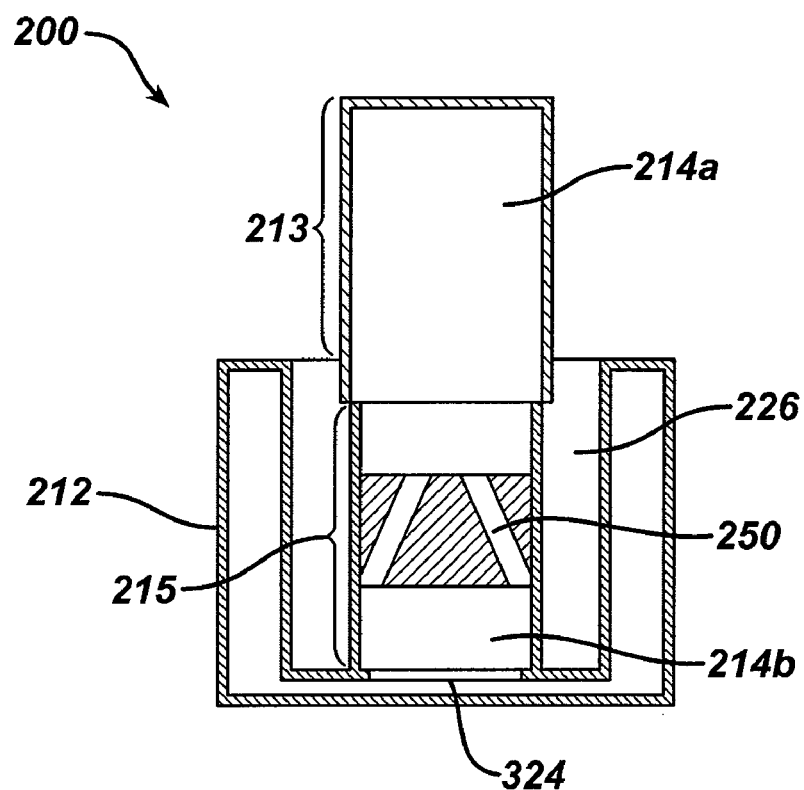
FIG. 9 is a cross-sectional view of another embodiment of a tissue collection device according to the present invention.

FIG. 9 illustrates a collection device 200 having a housing 212 with proximal and distal chambers 214a, 214b. The housing 212 includes two separate portions which form the proximal and distal chambers 214a, 214b. As shown, the proximal chamber 214a is formed within a proximal portion 213 of the housing 212, and the distal chamber 214b is formed within a distal portion 215 of the housing 212. The proximal housing 213 is slidably movable with respect to the distal chamber 214b and forms the driver mechanism. The device further includes a jet plate 250 that is disposed within the distal chamber 214b, and an overflow reservoir 226 for controlling the level of fluid within the distal chamber 214b. A tissue scaffold (not shown), and optionally a tissue retaining member, are adapted to be disposed between the proximal and distal chambers 214a, 214b.

In use, the proximal portion 213 is movable between a proximal position (as shown), in which the proximal chamber 214a is positioned apart from, but mated to, the distal chamber 214b, and a distal position (not shown), in which the proximal housing 213 is fully disposed around the distal housing 215. Movement of the proximal housing 213 from the distal position to the proximal position is effective to create a vacuum force within the chambers 214a, 214b and draw fluid from the distal chamber 214b up through a tissue scaffold disposed therebetween (not shown) and into the proximal chamber 214a. The force can be released by either removing the proximal housing 213 from the distal housing 215, or by providing an air flow port (not shown) in the proximal portion 213 of the housing 212.

Figure 10A:
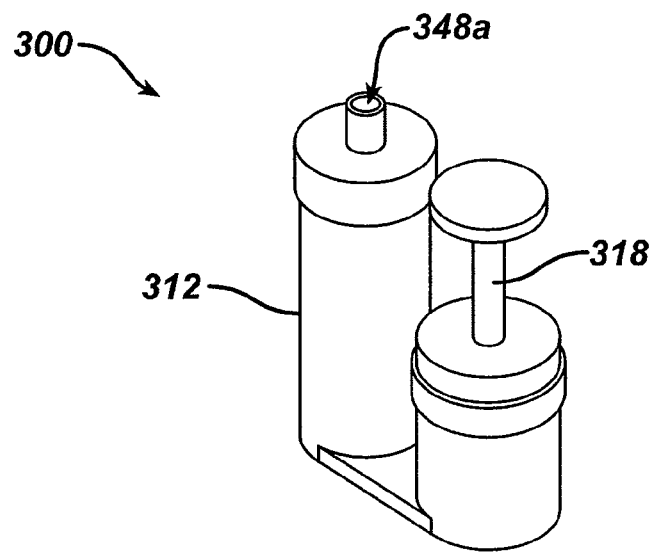
FIG. 10A is a perspective view of yet another embodiment of a tissue collection device according to the present invention.
Figure 10B:
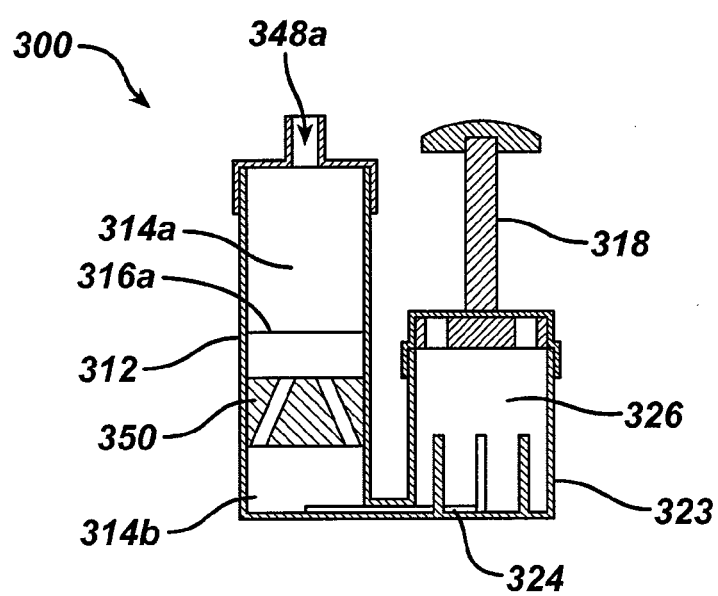
FIG. 10B is a cross-sectional view of the tissue collection device shown in FIG. 10A.

FIGS. 10A and 10B illustrate yet another embodiment of a tissue collection device 300 in which the plunger 318 is coupled to the distal chamber 314b and is effective to apply pressure to push, rather than pull, fluid up into the proximal chamber 314a. As shown, the collection device 300 includes a housing 312 having a tissue scaffold 316a disposed therein that separates an inner chamber of the housing 312 into a proximal chamber 314a and a distal chamber 314b. While not illustrated, the scaffold 316a can be disposed within a scaffold retaining member. The device 300 further includes a jet plate 350 disposed within the distal chamber 314b of the housing and that is effective to control the flow of fluid therethrough. Fluid can be introduced into the proximal chamber 314a through port 348a formed in the proximal end of the housing 312. A second housing 323 forms the overflow reservoir 326 and is coupled to the distal chamber 314b of housing 312 via a channel 324. A driver mechanism, e.g., plunger 318, is movably disposed within the second housing 323 and is effective to drive fluid disposed within the overflow reservoir 326 and the distal chamber 314b up through the jet plate 350 and the tissue scaffold 316a, and into the proximal chamber 314a. The force created by the plunger 318 can be released using a variety of techniques. The plunger 318, for example, can be adapted to allow fluid to flow therethrough when moved beyond a particular location in a distal direction. Alternatively, the plunger 318 can be pulled or allowed to return to the proximal position, thereby drawing fluid back through the scaffold and into the distal chamber 314b and the overflow reservoir 326.

Figure 11:
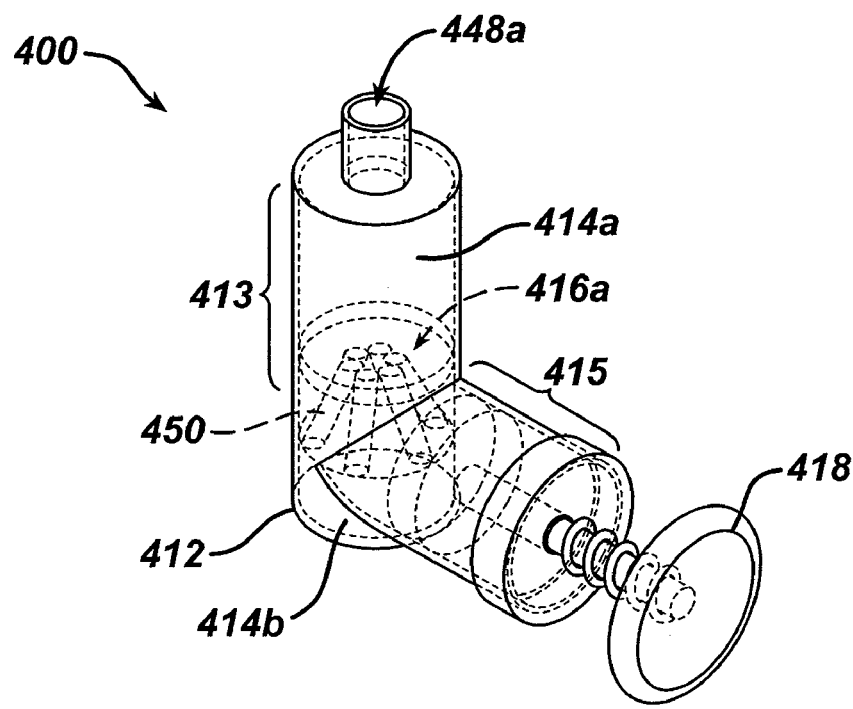
FIG. 11 is a perspective view of another embodiment of a tissue collection device according to the present invention.

FIG. 11 illustrates yet another embodiment of a tissue collection device 400 having a housing 412 with a proximal portion 413 and a distal portion 415, each having a substantially cylindrical shape. The distal portion 415 of the housing extends in a direction substantially transverse to the proximal portion 413, and includes a plunger 418 slidably disposed therein. The housing 412 further includes a tissue scaffold 416a disposed therein that separates the housing 412 into an inner proximal chamber 414a and an inner distal chamber 414b. The housing 412 further includes an inlet port 448a for introducing a tissue containing fluid into the proximal chamber 414a, and a jet plate 450 for controlling the flow of fluid therethrough. In use, the plunger 418, when slid into the distal portion 415 of the housing, is effective to push the fluid disposed within the distal chamber 414b up through the jet plate 450 and the tissue scaffold 416a into the proximal chamber 414a. The plunger 418 can then be retracted from the distal chamber 414b to draw the fluid back into the distal chamber 414b, thereby depositing the tissue back onto the tissue scaffold 416a. Alternatively, the device 400 can include an air flow valve or similar release mechanism to release the pressure within the chambers 414a, 414b and thereby allow the fluid to flow back into the distal chamber 414b.

Figure 12:
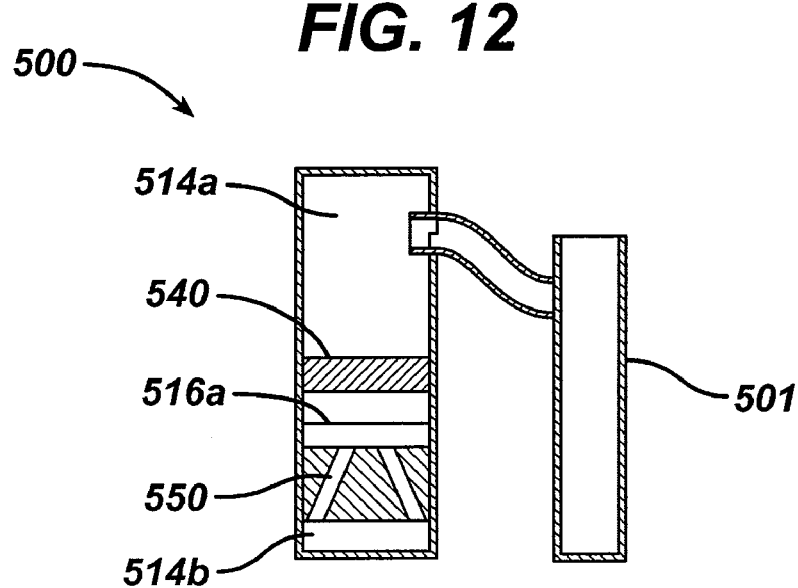
FIG. 12 is a perspective view of yet another embodiment of a tissue collection device according to the present invention.

In another embodiment, shown in FIG. 12, the collection device 500 utilizes a vacuum pump 501 to draw fluid up into the proximal chamber 514a from the distal chamber 514b. In this embodiment, the proximal chamber 514a includes the sealing member portion 540 of a plunger disposed therein. The vacuum pump 501 is coupled to the proximal chamber 514a such that the force of the pump 501 is effective to pull the sealing member 540 in a proximal direction, thereby drawing fluid from the distal chamber 514b up through the jet plate 550 and the scaffold 516a and into the proximal chamber 514a. The vacuum pump 501 can be released to allow the fluid to flow back down into the distal chamber 514b, thereby re-depositing the tissue back onto the tissue scaffold. While the vacuum pump 501 is shown coupled to the proximal chamber 514a, a person having ordinary skill in the art will appreciate that the vacuum pump can be coupled to the distal chamber 514b.

Figure 13A:
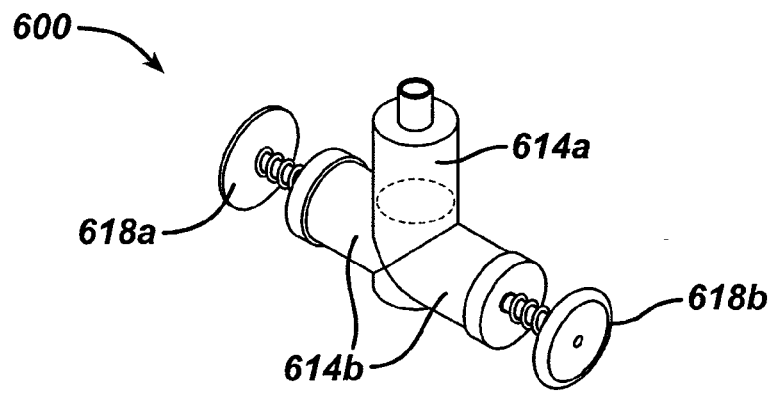
FIG. 13A is a perspective view of yet another embodiment of a tissue collection device according to the present invention.
Figure 13B:
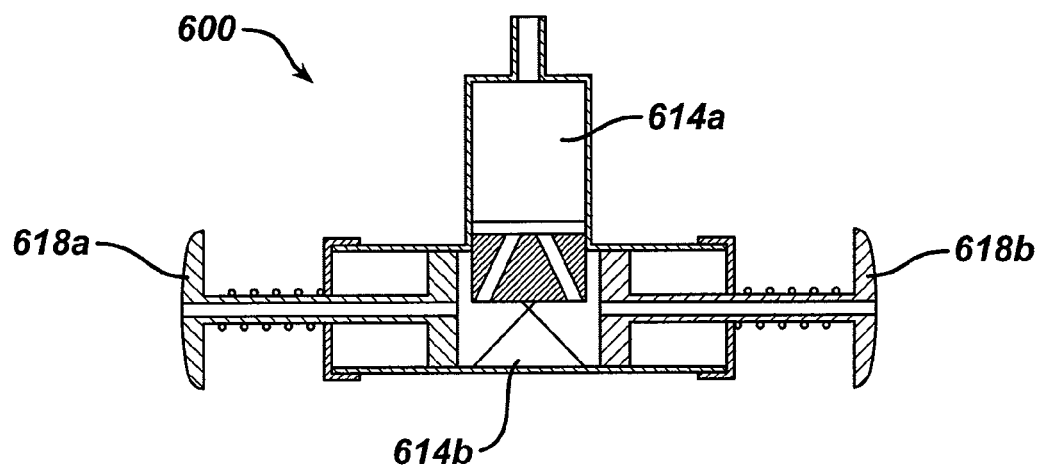
FIG. 13B is a cross-sectional view of the tissue collection device shown in FIG. 13A.

FIGS. 13A and 13B illustrate another embodiment of a tissue collection device 600 that is similar to device 400 shown in FIG. 11, but that includes opposed plungers 618a, 618b coupled to the distal chamber 614b. The device 600 operates substantially the same as device 400, except that both plungers 618a, 618b are utilized to push fluid up into the proximal chamber 614a.

The present invention also provides a method for preparing a tissue scaffold. The method includes the steps of providing a tissue collection device having a housing with a fluid-retaining inner chamber. A bioimplantable, fluid permeable tissue scaffold is disposed within the fluid-retaining inner chamber of the housing such that the tissue scaffold separates the fluid-retaining inner chamber into a first chamber and a second chamber. The device further includes a driver mechanism coupled to the housing and effective to create a force within the housing. Once the tissue scaffold is disposed within the housing, a tissue-containing fluid is delivered into the first chamber. The tissue containing fluid can be delivered by connecting the tissue collection device directly to a tissue biopsy and preparation device such as the device described in U.S. patent application Ser. No. 10/298,091, filed on Nov. 15, 2002, and entitled "Tissue Biopsy and Processing Device," which is expressly incorporated herein by reference in its entirety. Once the tissue containing fluid is introduced into the first chamber, the tissue is deposited onto the tissue scaffold and the fluid flows through the tissue scaffold and into the second chamber. The driver mechanism can then be activated to cause fluid to be displaced from the second chamber and into the first chamber. As a result, any tissue deposited on the tissue scaffold is dispersed within the fluid. The driver mechanism is then released to enable the fluid to return to the second chamber and thereby deposit the tissue onto the tissue scaffold. The device can also include a jet plate disposed within the second chamber for directing the flow of fluid from the second chamber to the proximal chamber, thereby causing the tissue disposed on the tissue scaffold to be more uniformly dispersed throughout the fluid. The jet plate is also effective to contact the tissue scaffold and force any air bubbles formed on the scaffold to flow up into the first chamber.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A biological tissue collection device, comprising:
a housing having a fluid-retaining inner chamber with a bioimplantable, fluid permeable tissue scaffold disposed therein such that the scaffold separates the fluid-retaining inner chamber into a first chamber and a second chamber, wherein the second chamber includes an overflow mechanism located just distal to the scaffold and effective to allow any excess fluid disposed within the second chamber to be released;
a driver mechanism coupled to the housing and effective to create a force within the housing to displace fluid disposed within the second chamber to the first chamber and thereby disperse any biological tissue deposited on the tissue scaffold within the fluid, wherein removal of the force enables the fluid to return to the second chamber and thereby deposit the biological tissue onto the tissue scaffold; and
a jet plate disposed within the second chamber and movable between an original position, in which the jet plate is positioned a distance apart from the first chamber, and a second position, in which the driver mechanism applies a force that causes the jet plate to move toward the first chamber, the jet plate being adapted to agitate fluid disposed within the second chamber as the jet plate moves between the original position and the second position such that biological tissue is uniformly deposited onto the tissue scaffold.

2. The biological tissue collection device of claim 1, wherein the jet plate, when disposed in the second position, is effective to apply pressure to a surface of the tissue scaffold to force any air bubbles formed on the tissue scaffold to flow into the first chamber.

3. The biological tissue collection device of claim 1, wherein the jet plate comprises a body having at least one channel extending therethrough for allowing fluid to flow through the jet plate.

4. The biological tissue collection device of claim 3, wherein the jet plate includes upper and lower surfaces, and wherein the at least one channel is oriented at an angle and extends between the upper and lower surfaces.

5. The biological tissue collection device of claim 4, wherein the at least one channel extends from a perimeter of the lower surface of the jet plate to a center of the upper surface of the jet plate.

6. The biological tissue collection device of claim 1, wherein the first chamber is disposed upstream of the tissue scaffold, and the second chamber is disposed downstream of the tissue scaffold.

7. The biological tissue collection device of claim 1, wherein the first chamber includes at least one entry port for delivering fluid into the first chamber.

8. The biological tissue collection device of claim 7, wherein the at least one entry port includes a flow control valve effective to control the flow of fluid therethrough.

9. The biological tissue collection device of claim 7, wherein the driver mechanism comprises a plunger coupled to the first chamber, and wherein the at least one entry port is formed through the plunger.

10. The biological tissue collection device of claim 1, wherein the driver mechanism is coupled to the first chamber and is effective to create a vacuum force to pull fluid from the second chamber into the first chamber.

11. The biological tissue collection device of claim 10, wherein the driver mechanism is selected from the group consisting of at least one plunger, a charged gas cylinder, and a vacuum pump.

12. The biological tissue collection device of claim 1, wherein the driver mechanism is coupled to the second chamber and is effective to create a force to push fluid from the second chamber into the first chamber.

13. The biological tissue collection device of claim 12, wherein the driver mechanism is selected from the group consisting of at least one plunger, a charged gas cylinder, and a vacuum pump.

14. The biological tissue collection device of claim 10, wherein the driver mechanism is formed integrally with the first chamber such that the first chamber is movable between a first position and a second position to create a vacuum force to draw fluid from the second chamber into the first chamber.

15. The biological tissue collection device of claim 1, wherein the overflow mechanism is selected from the group consisting of a channel, a port, and a valve.

16. The biological tissue collection device of claim 1, further comprising a retaining member effective to retain a tissue scaffold within the chamber.

17. The biological tissue collection device of claim 16, wherein the retaining member comprises a wire mesh disposed within the housing between the first and second chambers, the wire mesh being adapted to seat a tissue scaffold.

18. The biological tissue collection device of claim 16, wherein the retaining member comprises a clamping ring effective to clamp an outer perimeter of a tissue scaffold.

19. The biological tissue collection device of claim 16, wherein the retaining member is removably disposed within the inner chamber of the housing.

20. The biological tissue collection device of claim 19, wherein the housing includes a transverse slot formed therein for removably receiving the retaining member.

21. The biological tissue collection device of claim 19, wherein the housing comprises a first portion defining the first inner chamber, and a second portion defining the second inner chamber, the first and second portions being adapted to removably mate to one another and to receive a tissue scaffold therebetween.

22. The biological tissue collection device of claim 21, wherein the first and second portions define the retaining member.

23. The biological tissue collection device of claim 1, wherein the housing includes a proximal end, a distal end, and a sidewall extending therebetween and defining the fluid-retaining inner chamber, and wherein the first chamber is formed within a proximal portion of the housing, and the second chamber is formed within a distal portion of the housing.

24. The biological tissue collection device of claim 23, wherein the driver mechanism comprises a plunger disposed within the first chamber and movable between a first position, in which the plunger is positioned at a distal end of the first chamber, and a second position, in which the plunger is positioned adjacent the proximal end of the housing.

25. The biological tissue collection device of claim 24, wherein movement of the plunger from the first position to the second position is effective to create a vacuum within the fluid-retaining inner chamber of the housing to draw fluid disposed within the second chamber into the first chamber.

26. The biological tissue collection device of claim 25, further comprising a driver release mechanism coupled to the first chamber and effective to release the vacuum within the fluid-retaining inner chamber of the housing.

27. The biological tissue collection device of claim 26, wherein the driver release mechanism comprises an air flow entry port formed in the sidewall of the housing adjacent the proximal end of the housing and effective to allow air to enter the fluid-retaining inner chamber when the plunger is positioned proximal to the air flow entry port.

28. A biological tissue collection device, comprising:
a housing having a proximal chamber with at least one entry port for receiving fluid, a distal chamber, and a tissue scaffold retaining member disposed therebetween, wherein the distal chamber includes an overflow mechanism located just distal to the scaffold and effective to allow any excess fluid disposed within the distal chamber to be released;
a driver mechanism coupled to the proximal chamber and effective to create a fluid driving force within the proximal and distal chambers;
a driver release mechanism formed in one of the proximal distal chambers and that is effective to release the force applied by the driver mechanism; and
a jet plate movably disposed within the distal chamber that, when the driver mechanism is activated, is effective to agitate fluid disposed within the distal chamber to uniformly deposit biological tissue onto a tissue scaffold retained within the tissue scaffold retaining member.

29. The biological tissue collection device of claim 28, wherein the retaining member is removably disposed within the housing.

30. A method of preparing a tissue scaffold, comprising the steps of:

providing a biological tissue collection device having
a housing having a fluid-retaining inner chamber;
a bioimplantable, fluid permeable tissue scaffold disposed within the fluid-retaining inner chamber of the housing such that the tissue scaffold separates the fluid-retaining inner chamber into a first chamber and a second chamber, the second chamber including an overflow mechanism located just distal to the scaffold and effective to allow any excess fluid disposed within the second chamber to be released,
a driver mechanism coupled to the housing and effective to create a force within the housing, and
a jet plate disposed within the second chamber;
delivering a biological tissue-containing fluid into the first chamber, wherein the biological tissue is deposited onto the tissue scaffold and the fluid flows though the tissue scaffold and into the second chamber;
activating the driver mechanism to cause fluid to be displaced from the second chamber and into the first chamber, the driver mechanism causing the jet plate to agitate the fluid such that any biological tissue deposited on the tissue scaffold is dispersed within the fluid; and
releasing the driver mechanism to enable the fluid to return to the second chamber and thereby uniformly deposit the biological tissue onto the tissue scaffold.

31. The method of claim 30, wherein the driver mechanism is coupled to the first chamber and is effective to create a vacuum force to draw fluid from the second chamber into the first chamber.

32. The method of claim 30, wherein the driver mechanism is coupled to the second chamber and is effective to create a force to push fluid from the second chamber into the first chamber.

33. The method of claim 30, wherein the jet plate disposed within the second chamber moves between an original position, in which the jet plate is positioned a distance apart from the tissue scaffold, and a second position, in which the driver mechanism applies a force that causes the jet plate to contact the tissue scaffold.

34. The method of claim 33, wherein the jet plate applies a pressure to a surface of the tissue scaffold in the second position to compress any air bubbles formed on the tissue scaffold.

35. The method of claim 33, wherein the jet plate comprises a body having at least one channel extending therethrough, the fluid flowing though the channel in the jet plate.

36. The method of claim 30, further comprising releasing any excess fluid disposed within the second chamber through the overflow mechanism.

* * * * *